United States Patent [19]

Basu et al.

[11] Patent Number: 5,495,033
[45] Date of Patent: Feb. 27, 1996

[54] METHYLATED HERBICIDAL ADJUVANT

[75] Inventors: Hemendra N. Basu, Bartlett, Ill.; Joe V. Gednalske, Riverfalls, Wis.; Robert W. Herzfeld, Stillwater, Minn.

[73] Assignee: Cenex/Land O'Lakes Agronomy Company, Arden Hills, Minn.

[21] Appl. No.: 297,636

[22] Filed: Aug. 29, 1994

[51] Int. Cl.$^6$ .................................. C07C 53/126
[52] U.S. Cl. .................................. 554/1; 554/9
[58] Field of Search .................. 562/112, 113; 554/1, 9

[56] References Cited

U.S. PATENT DOCUMENTS

| | | | |
|---|---|---|---|
| 2,271,619 | 2/1942 | Bradshaw et al. | 260/410 |
| 2,360,844 | 10/1944 | Bradshaw et al. | 260/410.9 |
| 4,164,506 | 8/1979 | Kawahara et al. | 260/410.9 |
| 4,436,547 | 3/1984 | Sampson | 71/76 |
| 4,557,751 | 12/1985 | Ronning et al. | 71/91 |
| 4,695,411 | 9/1987 | Stern et al. | 260/410.9 |
| 4,698,186 | 10/1987 | Jeromin et al. | 260/421 |
| 4,867,972 | 9/1989 | Girardeau et al. | 424/81 |
| 4,956,286 | 9/1990 | Macrae | 435/134 |
| 4,971,630 | 11/1990 | Skaptason | 71/117 |
| 5,116,401 | 5/1992 | Young et al. | 71/86 |
| 5,118,338 | 6/1992 | Moller | 71/86 |
| 5,260,260 | 11/1993 | Gednalske et al. | 504/206 |

FOREIGN PATENT DOCUMENTS 957679  5/1964  United Kingdom.

OTHER PUBLICATIONS

Grossbord et al., *The Herbicide Glyphosate*, pp. 223–229 (1985).

Hoorne et al., *Novel Adjuvants for Agrochemical for Mediations Based on Sugar Ethers*, ICI Reprint RP67/91E. (1991).

*The Merck Index*, 10th Ed., Windholz et al. (editor), Merck & Co., Inc., pp. 1249 (1983).

*McCutcheon's Emulsifiers & Detergents*, McCutcheon Publishing Co., p. 192 (1990).

*The Agrochemicals Handbook*, 3rd Ed., Kidd et al., (editor), Royal Society of Chemistry (1991).

Puritch, *Pesticidal Soaps and Adjuvants—What are They and How do They Work?*, 23rd Annual Lower Mainland Horticultural Improvement Association Growers' Short Course, Feb. 11–13, 1981, pp. 53–66.

Van Valkenberg, *Adjuvants for Herbicides*, pp. i–ii, 1–8 (1979).

1992 *North Dakota Weed Control Research*, North Dakota University, pp. 65–71.

Choo et al., Conversion of Crude Palm Kernel Oil into its Methyl Esters on a Pilot Plant Seale, *Proceedings, World Conference on Oleochemicals: Into the 21st Century*, pp. 292–295, 1991.

*Primary Examiner*—Allen J. Robinson
*Assistant Examiner*—Brian G. Bembewick
*Attorney, Agent, or Firm*—Kinney & Lange

[57] ABSTRACT

The present invention includes a process for methylating free fatty acids in an acidulated soybean soapstock without altering a neutral oil component in the soybean soapstock. The present invention also includes a methylated acidulated soybean soapstock as well a herbicidal mixture that includes the methylated acidulated soybean soapstock.

1 Claim, 1 Drawing Sheet

METHYLATED HERBICIDAL ADJUVANT

BACKGROUND OF THE INVENTION

The present invention relates to a methylated acidulated soybean soapstock herbicidal adjuvant as well as a process for making the adjuvant, a herbicidal mixture that includes the adjuvant and a method for boosting herbicide performance.

Acidulated soybean soapstock is a waste product of soybean processing. The acidulated soybean soapstock is known as "foots" because the soapstock settles at the bottom of a tank collecting waste products from soybean oil processing. The term "foots" also connotes a historic non-utility of the product.

Acidulated soybean soapstock has had only a very limited utility because the acidulated soapstock includes water and impurities as well as some free fatty acids and neutral oil. These materials are not compatible with each other and interfere in extraction processes.

Acidulated soybean soapstock has been utilized as an ingredient in animal feed. In particular, the acidulated soybean soapstock has been used in feed for chickens, hogs, carp, and cockerels.

Acidulated soybean soapstock has also been described as an ingredient of a herbicidal mixture. The Gednalske et al. Patent, U.S. Pat. No. 5,260,260, issued Nov. 9, 1993, describes a mixture that includes acidulated soybean soapstock along with a number of specific herbicides in order to boost the performance of the herbicides.

Although acidulated soybean soapstock has had only limited usefulness, in general, lower alcohol esters of fatty acids have many industrial uses. Methyl and ethyl esters of fatty acids are gaining in importance for use as additives and substitutes to diesel fuel as well as for production of surface active agents and alcohol.

Fatty acid esters of lower alcohols are typically prepared by a transesterification reaction of neutral glycerides using alkaline catalysts such as described in the patents of Bradshaw, U.S. Pat. No. 2,271,619 and Meuly, U.S. Pat. No. 2,360,844. A direct esterification of fatty acids with methanol in a vapor phase using $KHSO_4$ has been described in Ruhrchemie, A. G., British Patent 957,679, issued May 15, 1964.

A use of potassium hydrogen sulfate, ammonium hydrogen sulfate and sulfonated ion exchange resin for the pre-esterification of fats and oils generally has been described by Y. M. Choo, K. Y. Cheah, A. N. Ma and A. Halim in Proceedings of World Conf. (1990) at 292–295. A process for a pre-esterification of free fatty acids in fats and oils using ion exchange resins has been described in U.S. Pat. No. 4,698,186, issued Oct. 6, 1987.

A combination of sulfuric acid and sulfonic acid has been described for esterification of fatty acids and glycerides using ethanol containing 7 to 30% by weight of water in U.S. Pat. No. 4,695,411, issued Sep. 22, 1987. A preparation of esters by esterification of fatty acids or glycerides with alcohols using an enzyme as a catalyst has been described in U.S. Pat. No. 4,956,286, issued Sep. 11, 1990.

The Kawahara et al. patent, U.S. Pat. No. 4,164,506, issued Aug. 14, 1979, describes production of lower alcohol esters of fatty acids by esterifying free fatty acids of unrefined fats having an acid value of 7.7 with a lower alcohol in an amount greater than the alcohol's solubility in the fats in a presence of an acid catalyst to make a product mixture. The product mixture is separated into a fat layer and a lower alcohol layer that may be removed. The fat layer is then subjected to an interesterification reaction between the resulting refined fat and a lower alcohol in the presence of an alkaline catalyst.

SUMMARY OF THE INVENTION

The process of the present invention for methylating an acidulated soybean soapstock includes providing an acidulated soybean soapstock. Next, the acidulated soybean soapstock is refluxed with methanol in a presence of sulfuric acid at a ratio of free fatty acids in the acidulated soybean soapstock to methanol of not more than about 1:2.5 w/w for a period of about 4 hours to form a methylated acidulated soybean soapstock mixture having methylated free fatty acids and unreacted neutral oil.

The present invention also includes an acidulated soybean soapstock mixture having methyl esters of free fatty acids and unreacted neutral oils. The present invention further includes a herbicidal mixture that includes the methylated acidulated soybean soapstock as well as a method for increasing herbicide performance that includes mixing the methylated acidulated soybean soapstock with the herbicide.

DETAILED DESCRIPTION OF THE PREFERRED EMBODIMENTS

Figure 1:
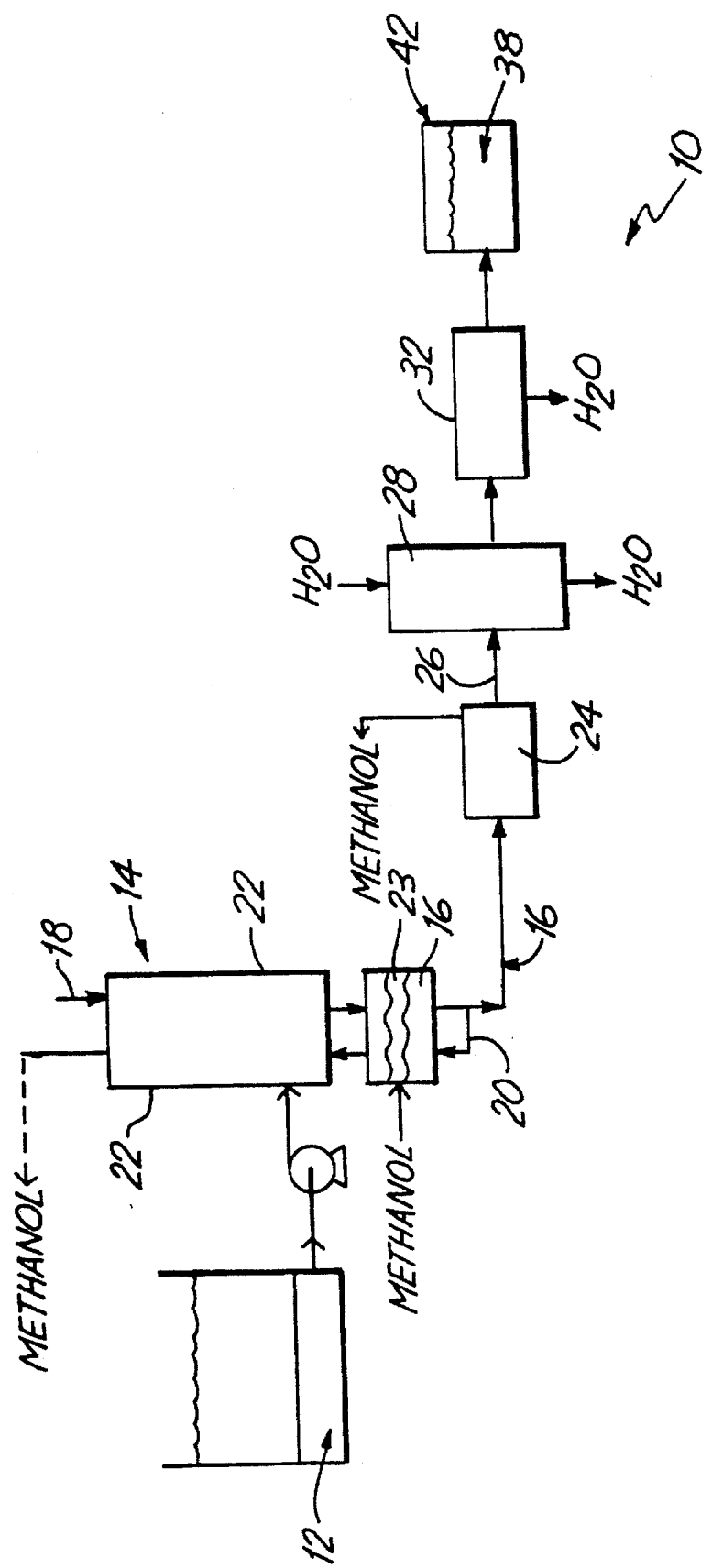
FIG. 1 shows a schematic diagram of the process for methylating free fatty acids in acidulated soybean soapstock without altering neutral oils in the soapstock.

The present invention includes a process for methylating at least about 99.5% of free fatty acids in acidulated soybean soapstock without methylating other constituents of the acidulated soybean soapstock. By the term "methylating an acidulated soybean soapstock" is meant that methyl esters of fatty acids in acidulated soybean soapstock are produced without forming reaction products with other components of the acidulated soybean soapstock. The methylating process, illustrated at 10 in FIG. 1, includes providing an acidulated soybean soapstock 12 having an acid value of at least about 80, refluxing the acidulated soybean soapstock with methanol and sulfuric acid in a reflux reaction vessel 14 for about 4 hours to form a methylated product 16, and drying the methylated acidulated soybean soapstock product. The present invention also includes a methylated acidulated soybean soapstock product that retains neutral oils and impurities of an unreacted acidulated soybean soapstock while including methylated free fatty acids of over 99.5% of free fatty acids in the unreacted acidulated soybean soapstock. The present invention additionally includes a herbicidal mixture having a methylated acidulated soybean soapstock ingredient as an adjuvant and finally includes a method for boosting herbicide performance by adding the methylated acidulated soybean soapstock to a herbicidal mixture.

That the acidulated soybean soapstock can be methylated to a degree of over 99.5% of free fatty acids is surprising because methylation of carboxylic acids is typically very difficult to accomplish to completion without particular process steps. These process steps include removing methylated carboxylic acids as they are formed in order to promote complete methylation of a feedstock. One other process step includes eliminating or at least reducing water within a system. The method of the present invention does not require either of these typically used steps in order to achieve an extraordinary degree of methylation of free fatty acids within the acidulated soybean soapstock. Exactly why and how the methylation is able to go substantially to completion is unknown.

Additionally, the process of the present invention methylates substantially all of the free fatty acids in acidulated soybean soapstock in a single one-step reaction. Typically, a mixture that includes both free fatty acids and neutral oil is subjected to a first hydrolysis step for the hydrolysis of neutral oil using a Twitchell process. Next, the free fatty acids are esterified with methanol using a Twitchell Reagent Catalyst. Alternatively, the free fatty acids may be esterified in a first reaction with glycerol followed by a second interesterification reaction.

That the free fatty acids in the acidulated soybean soapstock are methylated in a single step reaction without undesirable side reactions with the neutral oil or impurities of the acidulated soybean soapstock is remarkable. That undesirable side reactions are substantially eliminated results in a methylation process that is economical to perform because constituents of the acidulated soybean soapstock do not have to be extracted. The process of the present invention includes providing an acidulated soybean soapstock byproduct 12 of soybean oil refining processing. The acid value of the acidulated soybean soapstock is preferably about 86.1. However, acidulated soybean soapstock having an acid value within a range of 80 to 150 is suitable for use in the present invention. The acidulated soybean soapstock component that is provided and mixed to make the methylated adjuvant is typically a brown liquid and has a specific gravity of about 0.95.

The acidulated soybean soapstock used in the methylation reaction of the present invention is formed by the complete acidulation of soybean soapstock. Soybean soapstock is a byproduct of the alkali refining of soybean oil. In soybean oil processing, crude soybean oil is treated with dilute sodium hydroxide. In other acceptable embodiments, the crude soybean oil is treated with soda ash or a combination of sodium hydroxide and soda ash. The sodium hydroxide and soda ash react with free fatty acids in the crude soybean oil fraction to neutralize the free fatty acids and to form a soapstock. The soapstock is typically separated from the oil by centrifugation or settling. The soapstock is then treated with sulfuric acid in an acidulation step.

Soybean soapstock is about 6% of the total volume of crude soybean oil refined. The free fatty acids in acidulated soybean soapstock are typically less than about 1% of the total volume of crude soybean oil refined.

A contract grade of acidulated soybean soapstock preferably includes not less than about 85% total fatty acids by volume. Most preferably, the acidulated soybean soapstock used to make the methylated adjuvant of the present invention includes a total fatty acid concentration range of about 94% to 96% by volume as shown in Table 1. The acidulated soybean soapstock also includes a moisture concentration of not more than about 5% by volume. One typical analysis of acidulated soybean soapstock for use in the present invention, manufactured by the Honeymead Products Company of Mankato, Minn. is described in Table 1. One typical analysis of a fatty acid profile for acidulated soybean soapstock for use in the present invention is shown in Table 2.

TABLE 1

| Acid Value | 80–130 |
| Fatty Acids | 94%–96% |
| Color | Dark |
| Iodine | 118–130 |
| Moisture | (Carl-Fischer) 5% max |

TABLE 2

| Fatty Acid Profile | Percent of Total Fatty Acids |
| --- | --- |
| 14:0 myristic acid | 0.0 |
| 16:0 palmitic acid | 10.03 |
| 18:0 stearic acid | 3.82 |
| 18:1 oleic acid | 21.68 |
| 18:2 linoleic acid | 53.40 |
| 18:3 linolenic acid | 10.19 |
| 20:0 arachidic acid | 0.34 |
| 22:0 behenic acid | 0.28 |
| Miscellaneous | 0.26 |

All testing was performed by approved American Oil Chemists Society Methods.

The acidulated soybean soapstock provided is refluxed with methanol at a ratio of free fatty acid to methanol within a range of about 1:1 to about 1:2.5 w/w in the reflux reaction vessel 14. It is believed that the ratio of 1:2.5 is a maximum ratio of methanol to acidulated soybean soapstock required. Preferably, the methanol is anhydrous. The reflux reaction vessel 14 includes a liquid reflux stream 18, a vapor stream 20 and at least one stage 22.

The acidulated soybean soapstock is refluxed with methanol in the presence of sulfuric acid in a concentration of about 0.1% by weight for about 4 hours. The sulfuric acid feedstock concentration is about 96% w/w. The reflux temperature ranges from about 65° to 70° C. The sulfuric acid is added to a concentration of 0.1% by weight of the reflux mixture. The reaction is preferably performed in a vessel made of an acid resistant material, such as stainless steel.

Over the 4 hour reaction time interval, the progress of the reaction is periodically monitored by measuring the quantity of methylated fatty acids with a thin layer chromatography method that takes about 5 minutes to perform. The method includes applying a silica gel to a 5×20 plate. The reaction sample is applied to the silica gel and is transported with a solvent system that includes petroleum ether at 35°–60° C., ether and acetic acid in a ratio of 90:10:1 vol./vol./vol. The plates are developed by charring with a 50% sulfuric acid spray.

Once the methylation reaction has gone substantially to completion, the excess methanol is recovered using a rotary evaporator 24. The remaining methylation reaction product 26 is washed with hot water at a temperature of 93°–96° C. by liquid-liquid extraction in a wash kettle 28 and dried under vacuum 32. The vacuum may be formed with a vacuum pump (not shown) or with steam jet air injectors (not shown). The wash kettle 28 is preferably lined with glass. Once washed and dried, the methylated acidulated soybean soapstock 38 is stored in a tank 42.

Examples of the process of the present invention are described in Examples 1–4 described below. These examples are intended to provide illustration of steps for carrying out the process of the present invention but are not intended to limit the present invention.

EXAMPLE 1

A two liter, three necked flask equipped with a magnetic stirrer, a thermometer, a water condenser and a stopcock was charged with 200 gms of acidulated soapstock having an acid value 86.0, 700 gms anhydrous methanol and 18 mls concentrated sulfuric acid having a concentration of 96% by weight to form a mixture. The mixture was heated with agitation in a heated oil bath for 2 hours, initiating an esterification reaction.

The reaction was monitored by thin layer chromatography. The thin layer included silicagel applied on a 5×20 plate. The solvent system included petroleum ether at 35°–60° C. as well as ether and acetic acid in a ratio of 90:10:1, vol./vol./vol. The thin layer chromatography plates were developed by charring with a 50% sulfuric acid spray.

After cooling down the reaction mixture, a thick bottom layer was separated from a top layer. The bottom layer included the methyl esters and unreacted oil of the present invention. The top layer included excess methanol. The bottom layer was washed with hot water at 96° C. Any emulsion formed was broken by heating the oil layer to 93.3°–96.1° C. and then washing with hot water. This operation was repeated two times using 200 mls water each time or until the mixture of oil and ester was neutral. The methanol was removed from the top layer in a rotary evaporator and was washed twice with 200 of hot water. The yield of ester and oil mixture was 198 gms. Acid value was 0.6.

EXAMPLE 2

A quantity of 400 gms of acidulated soybean soapstock were reacted with 448 gms of anhydrous methanol and 17 gms of concentrated sulfuric acid catalyst forming a reaction mixture for 4 hours. At the end of the reaction, methanol was removed from the reaction mixture in a rotary evaporator. The reaction mixture was heated to 92° C. with 100 mls hot water. Once heated, the reaction mixture was washed with 250 mls of hot water at 93.3°–96.1° C., three times. The mixture was then dried under a vacuum of 27–28 inches of mercury forming a product. The yield of product was 390 gms. The analytical constants of the product were as follows: acid value 0.54; viscosity at 37.8° C., 8.52 Cst; flashpoint 185° C., specific gravity at 25° C. is 0.8976. Refractive index at 23.6° C. was 1.4646.

EXAMPLE 3

A three liter, three necked flask equipped with a magnetic stirrer, thermometer, reflux condenser and a nitrogen inlet was charged with 100 gms, of acidulated soybean soapstock, 340 gms of anhydrous methanol and 13 gms, 0.97% by weight, and concentrated sulfuric acid having a concentration of 96% by weight to form a mixture. The mixture was heated with a heating mantle and methanol and was refluxed at 65°–70° C. for a period of 6 hours. Samples were drawn at an interval of 2 hours to check the progress of the reaction using thin layer chromatography.

At the end of 6 hours, methanol was removed from the reaction mixture in a rotary evaporator. The reaction mixture was then transferred to a 3 liter beaker and heated to 95° C. in a nitrogen atmosphere with agitation using a magnetic stirrer. To this hot material, 350 mls of hot water 95° C. were added. The hot material was stirred for 2 minutes and was then allowed to settle. This operation was repeated three times to reduce the acidity of the mixture to neutral. Traces of water were removed under vacuum to form a product. The product yield was 1001 gms. The acid value of the product was 4.2 and flash point was 196° C.

This experiment illustrates that catalyst concentration may be increased to 2% by weight to get a complete reaction in shorter time. The amount of methanol used is in a molar ratio of 1:6, fatty acid:methanol.

EXAMPLE 4

To 500 gms of acidulated soybean soapstock were added 71 gms of anhydrous methanol and 2.5 gms, 0.43% by weight, concentrated sulfuric acid to form a mixture. The mixture was refluxed following the experimental procedures as described for Examples 1, 2 and 3. The reaction was carried out for 12 hours to form a reaction product. Examination of the reaction product indicated the presence of a large amount of unesterified fatty acids. Next, 71 gms of additional anhydrous methanol were added and a reaction was carried out for an additional 12 hours. At the end of the reaction, methanol was removed and a product was recovered after washing and drying. The acid value of the product was 2.96.

Even though 5 molar excess methanol was used for the reaction of Example 4, sulfuric acid concentration was important for the completion of the reaction in a shorter period of time. After methylation, the free fatty acid content of the methylated acidulated soybean soapstock product was only about 0.34% or less as percent oleic acid.

A thin layer chromatogram comparing unreacted acidulated soybean soapstock with the methylated acidulated soybean soapstock of methyl esters and neutral oil of the present invention demonstrated a presence of both methyl esters and neutral oil in comparable quantities to fatty acids and neutral oil in the unreacted starting material.

The methylated acidulated soybean soapstock adjuvant of the present invention performed as well or better than other herbicidal adjuvants tested. In particular, the methylated adjuvant of the present invention was tested in replicated research plots at two locations in 1993. Testing was conducted at one land grant university and by a herbicide manufacturer.

EXAMPLE 5

Field research trials of the methylated acidulated soybean soapstock adjuvant were conducted with herbicides that included imazethapyr and nicosulfuron. These herbicides were tested with the methylated seed adjuvant of the present invention identified as CL 7769 and 7745 and as shown in Tables 3 and 4. The identifications CL 7769 and 7745 differed in emulsifier type and emulsifier concentration added with the herbicide. However, the methylated soapstock concentration was the same for both CL 7769 and 7745 preparations. Other adjuvants tested included a 17% Crop Oil Concentrate (COC). The Crop Oil Concentrate is a standard petroleum based Crop Oil Concentrate. Another adjuvant included X-77®, a non-ionic alkylarylpolyoxyethylene surfactant manufactured by Valent U.S.A. Corp. of Walnut Creek, Calif. A third adjuvant included Sun-It II®, a standard methylated seed oil manufactured by AgSCo, Inc. of Grand Forks, N. Dak., commercially recommended for use with imazethapyr. A fourth adjuvant included the Preference® adjuvant manufactured by Cenex/Land O'Lakes of St. Paul, Minn., a soy-based non-ionic surfactant. The formulations also included a fertilizer addition of 28% liquid nitrogen (N).

The field trial was performed at the University of Wisconsin, River Falls location. The date of application of herbicide formulations was Jun. 9, 1993. Each of the formulations was applied with 17.2 gallons of water per acre with 8002 DG nozzles at 30 psi.

The weeds tested included giant foxtail (FT) having a height ranging from two to five inches, common lambsquarters (CL) having a height of four to twelve inches and a leaf number of four to five, and common ragweed (CR) having a leaf number of four to eight. The testing was performed with three replicates as shown in Tables 3 and 4.

The results for nicosulfuron are shown in Table 3. The results indicate that the methylated acidulated soybean soapstock formulation of the present invention worked at least as well as Crop Oil Concentrate, the X-77® and the Preference® adjuvants. In the case of common lambsquarters, the Crop Oil Concentrate had a kill of 92% compared to kills of 85% and 90% for the methylated acidulated soybean soapstock and herbicide formulations of the present invention. The common ragweed kill was 42% with the Crop Oil Concentrate formulation and was 35% and 65% with the methylated adjuvant, herbicide formulations of the present invention. The giant foxtail kill was 91% with Crop Oil Concentrate and ranged from 93% to 96% with the methylated acidulated soybean soapstock.

EXAMPLE 6

In a second trial at the University of Wisconsin, River Falls location, the herbicide imazethapyr was tested in conjunction with Sun-It II®, a methylated seed oil manufactured by AgSCo, Inc. of Grand Forks, N. Dak., 17% Crop Oil Concentrate, the methylated adjuvant of the present invention, 7769 and 7745, and Preference® manufactured by Cenex/Land O'Lakes of St. Paul, Minn. Nitrogen (N) was also added as a liquid fertilizer having a concentration of 28% N by volume. The application of the herbicidal mixtures was performed Jun. 9, 1993. A quantity of 17.2 gallons of water was added in conjunction with the herbicidal mixture with 8002 DG nozzles at 30 psi.

The weeds tested were foxtail (FT) having a height of two to five inches and lambsquarter having four to twelve leaves and a height of four to five inches. The results are shown in Table 4. As can be seen, in the case of foxtail, the adjuvant formulation of the present invention outperformed any other herbicidal adjuvant. In the case of lambsquarter, the methylated adjuvant of the present invention performed better than all other adjuvants except for the Preference® adjuvant.

TABLE 3

NICOSULFURON ON CORN
UNIVERSITY OF WISCONSIN-RIVERFALLS

| Treatment | Rate/AC | Rep I | | | Rep II | | | Rep III | | | Avg | | |
|---|---|---|---|---|---|---|---|---|---|---|---|---|---|
| | | CL | CR | FT | CL | CR | FT | CL | CR | FT | CL | CR | FT |
| Nicosulfuron | .67 ozs | 95 | 25 | 92 | 90 | 80 | 90 | 90 | 20 | 90 | 92 | 42 | 91 |
| 17% COC | 1.0% v/v | | | | | | | | | | | | |
| 28% N | 2.0 qts | | | | | | | | | | | | |
| Nicosulfuron | .67 ozs | 95 | 40 | 95 | 85 | 25 | 90 | 75 | 40 | 95 | 85 | 35 | 93 |
| CL 7769 | 1.0% v/v | | | | | | | | | | | | |
| 28% N | 2.0 qts | | | | | | | | | | | | |
| Nicosulfuron | .67 ozs | | | | | | | | | | | | |
| X-77 | .25% | 70 | 20 | 90 | 75 | 25 | 90 | 95 | 50 | 98 | 80 | 32 | 93 |
| 28% N | 2.0 qts | | | | | | | | | | | | |
| Nicosulfuron | .67 ozs | 85 | 45 | 95 | 92 | 55 | 90 | — | — | — | 89 | 50 | 93 |
| Preference ® | .25% | | | | | | | | | | | | |
| 28% N | 2.0 qts | | | | | | | | | | | | |
| Nicosulfuron | .67 ozs | 95 | 60 | 95 | 99 | 95 | 90 | 75 | 40 | 95 | 90 | 65 | 96 |
| CL 7745 | 1.0% | | | | | | | | | | | | |
| 28% N | 2.0 qts | | | | | | | | | | | | |

TABLE 4

IMAZETRAPYR ADDITIVE STUDY
UNIVERSITY OF WISCONSIN, RIVER FALLS

| Treatment | Rate/AC | Rep I | | Rep II | | Rep III | | Avg | |
|---|---|---|---|---|---|---|---|---|---|
| | | FT | LQ | FT | LQ | FT | LQ | FT | LQ |
| Imazethapyr | 4.0 ozs | 95 | 90 | 85 | 80 | 92 | 85 | 91 | 85 |
| Sun-It II ® | 1.5 pts | | | | | | | | |
| 28% N | 1.0 qts | | | | | | | | |
| Imazethapyr | 4.0 ozs | 95 | 90 | 90 | 65 | 75 | 55 | 87 | 70 |
| 17% COC | 1.0 qts | | | | | | | | |
| 28% N | 1.0 qts | | | | | | | | |
| Imazethapyr | 4.0 ozs | 99 | 95 | 95 | 90 | 95 | 90 | 96 | 92 |
| CL 7769 | 1.5 pts (RP-13) | | | | | | | | |
| 28% N | 1.0 qts | | | | | | | | |
| Imazethapyr | 4.0 ozs | 95 | 85 | 90 | 60 | 95 | 70 | 93 | 72 |

TABLE 4-continued

IMAZETRAPYR ADDITIVE STUDY
UNIVERSITY OF WISCONSIN, RIVER FALLS

| Treatment | Rate/AC | Rep I FT | Rep I LQ | Rep II FT | Rep II LQ | Rep III FT | Rep III LQ | Avg FT | Avg LQ |
|---|---|---|---|---|---|---|---|---|---|
| X-77 | .25% | | | | | | | | |
| 28% N | 1.0 qts | | | | | | | | |
| Imazethapyr | 4.0 ozs | 98 | 85 | 95 | 95 | 99 | 95 | 97 | 92 |
| Preference ® | .25% | | | | | | | | |
| 28% N | 1.0 qts | | | | | | | | |
| Imazethapyr | 4.0 ozs | 99 | 95 | 75 | 90 | 85 | 80 | 86 | 88 |
| CL 7745 | 1.5 pts | | | | | | | | |
| 28% N | 1.0 qts | | | | | | | | |

EXAMPLE 7

Additional testing of the adjuvant of the present invention was performed at a test area on a Land O'Lakes research farm in Hamilton County, Iowa. The test area was planted with bulk corn in 1992. Nitrogen as urea was applied in April and October of 1992. No pesticides were applied in 1992. The test area was disked and V-ripped in the late fall.

In 1993, the only pesticides applied to the study area were the test pesticides. No cultivation or other maintenance procedures were performed. A quality of 160 units of nitrogen as urea was applied in each of April and December of 1993. Weeds that included tame millet, volunteer corn and common lambsquarter were seeded and incorporated with a roterra.

The test area was a randomized complete block with four replications. A plot size included four 30 inch rows, 12 feet wide, including a 2 foot running check, by 25 feet long. The test area was planted Jun. 22, 1993, with soybeans at approximately 149,000 seeds per acre.

Herbicidal mixtures were applied Jul. 21, 1993, with a tractor mounted hooded broom at 2 mph. The mixtures were applied with spray nozzles, 8002 DG, at 30 psi propelled by compressed air. The rate of application was 3,000 mls per 1,120 square feet. The herbicidal carrier was water at a pH of about 7.4. The atmospheric temperature was 24° C. The sky was mostly cloudy with a southeast wind at about 15 mph. The crop stage at application was third trifoliate.

The stage of common sunflower weed was 2 feet tall, with 2–10 plants per plot. Redroot pigweed was 18 inches tall with 1 plant per about 1 square foot. Giant foxtail was 12 inches tall with 10 plants per 1 square foot. Volunteer corn was present in a quality of about 1 plant per 1 square foot. The herbicidal mixtures were applied to the test area immediately after mixing.

The herbicidal mixtures tested included the adjuvants Sun-It II®, Crop Oil Concentrate (COC), X-77®, and Preference® adjuvants, such as described above. The designation 7712 refers to the methylated acidulated soybean soapstock of the present invention. The designation C44769 refers to a commercially available methylated seed oil manufactured by the Henkel Corp. of Cincinnati, Ohio. The designation, Scoil®, refers to a methylated seed oil manufactured by AgSCo, Inc. of Grand Forks, N. Dak. The designations CL 7379 and CL 7435 refer to experimental non-ionic surfactants of Cenex/Land O'Lakes. The designation CL 2513 refers to a methylated soybean oil methylated in accordance with conventional methods and blended with the same emulsifier as in CL 7769. The designation, Preference II® had the same ingredients as Preference® and in addition included a viscosity reducing agent.

The herbicidal mixtures were tested with respect to injury caused to the soybean plant as well as weed control. The injury was rated on a scale of 0 to 100 as described in Table 5. The degree of weed control was measured on a scale of 0 to 100 such as is described in Table 6. The performance of the herbicidal mixtures was measured at 7 days after treatment, 14 days after treatment, and 28 days after treatment. It was observed that the entire test area suffered due to excessively wet weather.

TABLE 5

| Rating | Main Description | Detailed Description |
|---|---|---|
| 0 | No effect | No crop reduction or injury |
| 10 | Slight effect | Slight crop discoloration or stunting |
| 20 | | Some crop discoloration or stunt loss |
| 30 | | Crop injury more pronounced but not lasting |
| 40 | Moderate effect | Moderate injury, crop usually recovers |
| 50 | | Crop injury more lasting, recovery doubtful |
| 60 | | Lasting crop injury, no recovery |
| 70 | Severe effect | Heavy crop injury and stand loss |
| 80 | | Crop nearly destroyed - A few surviving plants |
| 90 | | Only occasional live crop plants left |
| 100 | Complete effect | Complete crop destruction |

TABLE 6

| Rating | Main Description | Detailed Description |
|---|---|---|
| 0 | No effect | No weed control |
| 10 | Slight effect | Very poor weed control |
| 20 | | Poor weed control |
| 30 | | Poor to deficient weed control |
| 40 | Moderate effect | Deficient weed control |
| 50 | | Deficient to moderate weed control |
| 60 | | Moderate weed control |
| 70 | Severe effect | Weed control somewhat less than satisfactory |
| 80 | | Satisfactory to good weed control |
| 90 | | Very good to excellent weed control |
| 100 | Complete effect | Complete weed destruction |

The herbicidal mixtures included mixtures with the herbicide imazethapyr. The rate of application of the imazethapyr was 4 ounces (oz.) per acre for all tests. Adjuvants added to the imazethapyr included Sun-It II® added at a concentration of 1.5 pints (pts.) per acre and a mixture having 28% nitrogen by volume added at a concentration of 1 quart (qt.) per acre. The adjuvant of the present invention was added with imazethapyr at a concentration of 1.5 pts. per acre and 28% nitrogen at a concentration of 1 qt. per acre. Crop Oil Concentrate of a concentration of 17% was added at a rate of 1.5 pts. per acre with a 28% nitrogen mixture at a concentration of 1 qt. per acre. The nonionic surfactant, X-77®, was added at a concentration of 0.25% volume surfactant/volume water and a mixture of 28% nitrogen at a rate of 1 qt. per acre. Preference® formulations were added at a concentration of 0.25% volume/volume water with a mixture having 28% nitrogen volume/volume at a concentration of 1 qt. per acre.

The percent injury of these herbicidal mixtures one week after treatment (1 WAT) on soybeans is shown in Table 7. As can be seen, the combination of the imazethapyr, Sun-It II®, and nitrogen caused significantly more injury than other herbicidal mixtures. However, the amount of injury was not very high, at 13.75%.

TABLE 7

% Injury Based on The 0–100 Scale I WAT

| Treat | Herbicide Treatments | Rate/Acre | Time | Injury | Alpha = 0.05[a] | Alpha = 0.1[a] |
|---|---|---|---|---|---|---|
| 1 | Imazethapyr + Sun-It II ® + 28% N | 4 oz + 1.5 pt + 1 qt | Post | 13.75 | a | a |
| 2 | Imazethapyr + CL4769 + 28% N | 4 oz + 1.5 pt + 1 qt | Post | 7.50 | b | bc |
| 3 | Imazethapyr + CL7769 + 28% N | 4 oz + 1.5 pt + 1 qt | Post | 6.25 | b | bc |
| 4 | Imazethapyr + 17% COC + 28% N | 4 oz + 1.5 pt + 1 qt | Post | 6.25 | b | bc |
| 5 | Imazethapyr + X-77 ® + 28% N | 4 oz + 0.25% v/v + 1 qt | Post | 6.25 | b | bc |
| 6 | Imazethapyr + Preference ® + 28% N | 4 oz + 0.25% v/v + 1 qt | Post | 5.00 | b | c |
| 7 | Imazethapyr + PreferenceII ® + 28% N | 4 oz + 0.25% v/v + 1 qt | Post | 5.00 | b | c |
| 8 | Imazethapyr + CL7379 + 28% N | 4 oz + 0.25% v/v + 1 qt | Post | 7.50 | b | bc |
| 9 | Imazethapyr + CL7435 + 28% N | 4 oz + 0.25% v/v + 1 qt | Post | 10.00 | ab | ab |
| 10 | Imazethapyr + PREFER-28 ® | 4 oz + 2.8% v/v | Post | 6.25 | b | bc |
| 11 | Imazethapyr + CL7712 + 28% N | 4 oz + 1.5 pt + 1 qt | Post | 6.25 | b | bc |
| 12 | Imazethapyr + CL2513 + 28% N | 4 oz + 1.5 pt + 1 qt | Post | 6.25 | b | bc |
| | | | Isd = 0.5 | | 5.06 | |
| | | | Isd = .1 | | | 4.21 |
| | | | C.V. | 48.972 | | |

The percent of common sunflower weed control based on the 0 to 100 scale is shown in Tables 8A and 8B. Sunflower control tended to be very good for all treatments.

TABLE 8A

% Sunflower Control Based on The 0–100 Scale

| | | | | 2 WAT | | |
|---|---|---|---|---|---|---|
| Treat | Herbicide Treatments | Rate/Acre | Time | Cosf | Alpha = 0.05 | Alpha = 0.1 |
| 1 | Imazethapyr + Sun-It II ® + 28% N | 4 oz + 1.5 pt + 1 qt | Post | 98.75 | a | a |
| 2 | Imazethapyr + CL4769 + 28% N | 4 oz + 1.5 pt + 1 qt | Post | 97.25 | a | a |
| 3 | Imazethapyr + CL7769 + 28% N | 4 oz + 1.5 pt + 1 qt | Post | 99.50 | a | a |
| 4 | Imazethapyr + 17% COC + 28% N | 4 oz + 1.5 pt + 1 qt | Post | 99.25 | a | a |
| 5 | Imazethapyr + X-77 ® + 28% N | 4 oz + 0.25% v/v + 1 qt | Post | 97.75 | a | a |
| 6 | Imazethapyr + Preference ® + 28% N | 4 oz + 0.25% v/v + 1 qt | Post | 100.00 | a | a |
| 7 | Imazethapyr + PreferenceII ® + 28% N | 4 oz + 0.25% v/v + 1 qt | Post | 97.75 | a | a |
| 8 | Imazethapyr + CL7379 + 28% N | 4 oz + 0.25% v/v + 1 qt | Post | 83.25 | b | b |
| 9 | Imazethapyr + CL7435 + 28% N | 4 oz + 0.25% v/v + 1 qt | Post | 98.25 | a | a |
| 10 | Imazethapyr + PREFER-28 ® | 4 oz + 2.8% v/v | Post | 100.00 | a | a |
| 11 | Imazethapyr + CL7712 + 28% N | 4 oz + 1.5 pt + 1 qt | Post | 100.00 | a | a |
| 12 | Imazethapyr + CL2513 + 28% N | 4 oz + 1.5 pt + 1 qt | Post | 100.00 | a | a |
| | | | Isd = 0.5 | | 11.79 | |
| | | | Isd = .1 | | | 9.80 |
| | | | C.V. | 8.39 | | |

TABLE 8B

% Sunflower Control Based on The 0–100 Scale

|   |   |   |   | 4 WAT | | |
|---|---|---|---|---|---|---|
| Treat | Herbicide Treatments | Rate/Acre | Time | Cosf | Alpha = 0.05 | Alpha = 0.1 |
| 1 | Imazethapyr + Sun-It II ® + 28% N | 4 oz + 1.5 pt + 1 qt | Post | 100.00 | a | a |
| 2 | Imazethapyr + CL4769 + 28% N | 4 oz + 1.5 pt + 1 qt | Post | 92.50 | b | b |
| 3 | Imazethapyr + CL7769 + 28% N | 4 oz + 1.5 pt + 1 qt | Post | 95.00 | ab | ab |
| 4 | Imazethapyr + 17% COC + 28% N | 4 oz + 1.5 pt + 1 qt | Post | 96.75 | ab | ab |
| 5 | Imazethapyr + X-77 ® + 28% N | 4 oz + 0.25% v/v + 1 qt | Post | 96.25 | ab | ab |
| 6 | Imazethapyr + Preference ® + 28% N | 4 oz + 0.25% v/v + 1 qt | Post | 100.00 | a | a |
| 7 | Imazethapyr + PreferenceII ® + 28% N | 4 oz + 0.25% v/v + 1 qt | Post | 97.50 | ab | ab |
| 8 | Imazethapyr + CL7379 + 28% N | 4 oz + 0.25% v/v + 1 qt | Post | 92.50 | b | b |
| 9 | Imazethapyr + CL7435 + 28% N | 4 oz + 0.25% v/v + 1 qt | Post | 97.50 | ab | ab |
| 10 | Imazethapyr + PREFER-28 ® | 4 oz + 2.8% v/v | Post | 95.00 | ab | ab |
| 11 | Imazethapyr + CL7712 + 28% N | 4 oz + 1.5 pt + 1 qt | Post | 98.00 | ab | ab |
| 12 | Imazethapyr + CL2513 + 28% N | 4 oz + 1.5 pt + 1 qt | Post | 98.75 | ab | a |
|   |   |   | lsd = 0.5 |   | 6.82 |   |
|   |   |   | lsd = .1 |   |   | 5.67 |
|   |   |   | C.V. | 4.91 |   |   |

The percent of giant foxtail weed control based on the scale of 0 to 100 is shown in Tables 9A and 9B. Generally, giant foxtail control was very good. The performance of the present invention was particularly good having a percent control over 90%.

EXAMPLE 8

In Example 8, a number of different herbicidal mixtures were examined for their effect on controlling weeds in soybeans. The test location and test conditions were substantially the same as conditions described in Example 7. The herbicidal mixtures were applied at a rate of 3,000 mls per 1,120 square feet. The surfactant equivalents are as follows: 0.25% v/v=0.308 qts. per acre; 0.5% v/v=0.616 qts. per acre; 1% v/v=1.233 qts. per acre.

TABLE 9A

% Giant Foxtail Control Based on The 0–100 Scale

|   |   |   |   | 2 WAT | | |
|---|---|---|---|---|---|---|
| Treat | Herbicide Treatments | Rate/Acre | Time | Gift | Alpha = 0.05 | Alpha = 0.1 |
| 1 | Imazethapyr + Sun-It II ® + 28% N | 4 oz + 1.5 pt + 1 qt | Post | 96.50 | a | a |
| 2 | Imazethapyr + CL4769 + 28% N | 4 oz + 1.5 pt + 1 qt | Post | 92.75 | a | ab |
| 3 | Imazethapyr + CL7769 + 28% N | 4 oz + 1.5 pt + 1 qt | Post | 92.75 | a | ab |
| 4 | Imazethapyr + 17% COC + 28% N | 4 oz + 1.5 pt + 1 qt | Post | 95.25 | a | ab |
| 5 | Imazethapyr + X-77 ® + 28% N | 4 oz + 0.25% v/v + 1 qt | Post | 92.75 | a | ab |
| 6 | Imazethapyr + Preference ® + 28% N | 4 oz + 0.25% v/v + 1 qt | Post | 84.50 | a | ab |
| 7 | Imazethapyr + PreferenceII ® + 28% N | 4 oz + 0.25% v/v + 1 qt | Post | 89.00 | a | ab |
| 8 | Imazethapyr + CL7379 + 28% N | 4 oz + 0.25% v/v + 1 qt | Post | 86.50 | a | ab |
| 9 | Imazethapyr + CL7435 + 28% N | 4 oz + 0.25% v/v + 1 qt | Post | 92.50 | a | ab |
| 10 | Imazethapyr + PREFER-28 ® | 4 oz + 2.8% v/v | Post | 94.00 | a | ab |
| 11 | Imazethapyr + CL7712 + 28% N | 4 oz + 1.5 pt + 1 qt | Post | 96.50 | a | a |
| 12 | Imazethapyr + CL2513 + 28% N | 4 oz + 1.5 pt + 1 qt | Post | 82.75 | a | b |
|   |   |   | lsd = 0.5 |   | 16.01 |   |
|   |   |   | lsd = .1 |   |   | 13.32 |
|   |   |   | C.V. | 12.19 |   |   |

TABLE 9B

% Giant Foxtail Based on The 0–100 Scale

| | | | | | 4 WAT | |
|---|---|---|---|---|---|---|
| Treat | Herbicide Treatments | Rate/Acre | Time | Gift | Alpha = 0.05 | Alpha = 0.1 |
| 1 | Imazethapyr + Sun-It II ® + 28% N | 4 oz + 1.5 pt + 1 qt | Post | 91.25 | a | a |
| 2 | Imazethapyr + CL4769 + 28% N | 4 oz + 1.5 pt + 1 qt | Post | 91.25 | a | a |
| 3 | Imazethapyr + CL7769 + 28% N | 4 oz + 1.5 pt + 1 qt | Post | 82.50 | ab | a |
| 4 | Imazethapyr + 17% COC + 28% N | 4 oz + 1.5 pt + 1 qt | Post | 85.00 | a | a |
| 5 | Imazethapyr + X-77 ® + 28% N | 4 oz + 0.25% v/v + 1 qt | Post | 85.00 | a | a |
| 6 | Imazethapyr + Preference ® + 28% N | 4 oz + 0.25% v/v + 1 qt | Post | 82.50 | ab | a |
| 7 | Imazethapyr + PreferenceII ® + 28% N | 4 oz + 0.25% v/v + 1 qt | Post | 82.50 | ab | a |
| 8 | Imazethapyr + CL7379 + 28% N | 4 oz + 0.25% v/v + 1 qt | Post | 75.50 | a | a |
| 9 | Imazethapyr + CL7435 + 28% N | 4 oz + 0.25% v/v + 1 qt | Post | 82.50 | ab | a |
| 10 | Imazethapyr + PREFER-28 ® | 4 oz + 2.8% v/v | Post | 72.50 | b | b |
| 11 | Imazethapyr + CL7712 + 28% N | 4 oz + 1.5 pt + 1 qt | Post | 91.25 | a | a |
| 12 | Imazethapyr + CL2513 + 28% N | 4 oz + 1.5 pt + 1 qt | Post | 88.75 | a | a |
| | | | lsd = 0.5 | | 11.92 | |
| | | | lsd = .1 | | | 9.91 |
| | | | C.V. | 9.72 | | |

The herbicidal mixtures were applied when the crop was in the fourth trifoliate stage. The volunteer corn was V6 at a concentration of 1 plant per 1 square foot. The giant foxtail was 12 inches tall with 7 plants per square foot. The evaluation for injury and weed control was the same as described for Example 7. The entire test area suffered due to excessively wet weather. Yellow foxtail, green foxtail and tame millet populations never developed and could not be scored.

Herbicidal mixtures are shown in Tables 10A and 10B. The herbicides included sethoxydim, quizalofop, fluzifop and fenoxoprop, and clethodim. Each of these herbicides was combined with 17% Crop Oil Concentrate in a concentration of 1% v/v, Scoil® in a concentration of 1% v/v, Sun-It II® in a concentration of 1% v/v, the adjuvants of the present invention in a concentration of 1% v/v, Preference® in a concentration of 0.25% v/v and X-77® in a concentration of 0.25% v/v. The percent volunteer corn control based on the 0 to 100 scale is shown in Tables 10A and 10B. As can be seen, sethoxydim herbicide performance was the worst. However, the adjuvant of the present invention in combination with the sethoxydim had a performance that was well over 90%. The percent giant foxtail control of the herbicidal mixtures described is shown in Tables 11A and 11B. Once again, the sethoxydim treatments tended to poorer than the performance of other herbicides tested.

TABLE 10A

% Volunteer Corn Control

| | | | | 2 WAT | | |
|---|---|---|---|---|---|---|
| Treat | Herbicide Treatments | Rate/Acre | Time | Voco | Alpha = 0.05 | Alpha = 0.1 |
| 1 | Sethoxydim + 17% COC | 12 oz + 1% v/v | Post | 98.00 | c–f | d–f |
| 2 | Sethoxydim + Scoil ® | 12 oz + 1% v/v | Post | 97.25 | d–f | e–g |
| 3 | Sethoxydim + Sun-It II ® | 12 oz + 1% v/v | Post | 98.25 | b–e | c–f |
| 4 | Sethoxydim + CL4769 | 12 oz + 1% v/v | Post | 99.50 | a–c | a–c |
| 5 | Sethoxydim + CL7769 | 12 oz + 1% v/v | Post | 96.50 | f | g |
| 6 | Sethoxydim + Preference ® | 12 oz + 0.25% v/v | Post | 98.25 | b–e | c–f |
| 7 | Sethoxydim + Preference ® | 12 oz + 0.5% v/v | Post | 97.25 | d–f | e–g |
| 8 | Sethoxydim + X-77 ® | 12 oz + 0.25% v/v | Post | 98.00 | c–f | d–f |
| 9 | Quizalofop + 17% COC | 5 oz + 1% v/v | Post | 100.00 | a | a |
| 10 | Quizalofop + Scoil ® | 5 oz + 1% v/v | Post | 100.00 | a | a |
| 11 | Quizalofop + Sun-It II ® | 5 oz + 1% v/v | Post | 100.00 | a | a |
| 12 | Quizalofop + CL4769 | 5 oz + 1% v/v | Post | 100.00 | a | a |
| 13 | Quizalofop + CL7769 | 5 oz + 1% v/v | Post | 99.25 | a–c | a–d |
| 14 | Quizalofop + Preference ® | 5 oz + 0.25% v/v | Post | 99.00 | a–c | a–d |
| 15 | Quizalofop + Preference ® | 5 oz + 0.5% v/v | Post | 99.75 | ab | ab |
| 16 | Ouizalofop + X-77 ® | 5 oz + 0.25% v/v | Post | 99.50 | a–c | a–c |
| 17 | Fluzifop + Fenoxoprop + 17% COC | 6 oz + 1% v/v | Post | 99.00 | a–c | a–d |
| 18 | Fluzifop + Fenoxoprop + Scoil ® | 6 oz + 1% v/v | Post | 99.50 | a–c | a–c |
| 19 | Fluzifop + Fenoxoprop + Sun-It II ® | 6 oz + 1% v/v | Post | 99.00 | a–c | a–d |
| 20 | Fluzifop + Fenoxoprop + CL4769 | 6 oz + 1% v/v | Post | 99.25 | a–c | a–d |
| 21 | Fluzifop + Fenoxoprop + CL7769 | 6 oz + 1% v/v | Post | 99.00 | a–c | a–d |
| 22 | Fluzifop + Fenoxoprop + Preference ® | 6 oz + 0.25% v/v | Post | 100.00 | a | a |
| 23 | Fluzifop + Fenoxoprop + Preference ® | 6 oz + 0.5% v/v | Post | 98.50 | a–e | b–e |
| 24 | Fluzifop + Fenoxoprop + X-77 ® | 6 oz + 0.25% v/v | Post | 100.00 | a | a |
| 25 | Clethodim + 17% COC | 4 oz + 1% v/v | Post | 99.00 | a–c | a–d |
| 26 | Clethodim + Scoil ® | 4 oz + 1% v/v | Post | 99.00 | a–c | a–d |
| 27 | Clethodim + Sun-It II ® | 4 oz + 1% v/v | Post | 100.00 | a | a |
| 28 | Clethodim + CL4769 | 4 oz + 1% v/v | Post | 98.75 | a–d | a–d |
| 29 | Clethodim + CL7769 | 4 oz + 1% v/v | Post | 99.50 | a–c | a–c |
| 30 | Clethodim + Preference ® | 4 oz + 0.25% v/v | Post | 97.00 | ef | fg |
| 31 | Clethodim + Preference ® | 4 oz + 0.5% v/v | Post | 97.25 | d–f | e–g |
| 32 | Clethodim + X-77 ® | 4 oz + 0.25% v/v | Post | 98.00 | c–f | d–f |
| | | | lsd = 0.5 | | 1.734 | |
| | | | lsd = .1 | | | 1.451 |
| | | | C.V. | 1.249 | | |

TABLE 10B

% Volunteer Corn Control

| | | | | 4 WAT | | |
|---|---|---|---|---|---|---|
| Treat | Herbicide Treatments | Rate/Acre | Time | Voco | Alpha = 0.05 | Alpha = 0.1 |
| 1 | Sethoxydim + 17% COC | 12 oz + 1% v/v | Post | 65.00 | bc | c |
| 2 | Sethoxydim + Scoil ® | 12 oz + 1% v/v | Post | 94.25 | a | a |
| 3 | Sethoxydim + Sun-It II ® | 12 oz + 1% v/v | Post | 95.25 | a–e | b–f |
| 4 | Sethoxydim + CL4769 | 12 oz + 1% v/v | Post | 67.50 | bc | a |
| 5 | Sethoxydim + CL7769 | 12 oz + 1% v/v | Post | 95.25 | a | a |
| 6 | Sethoxydim + Preference ® | 12 oz + 0.25% v/v | Post | 96.50 | a | a |
| 7 | Sethoxydim + Preference ® | 12 oz + 0.5% v/v | Post | 64.25 | cd | c |
| 8 | Sethoxydim + X-77 ® | 12 oz + 0.25% v/v | Post | 55.00 | d | d |
| 9 | Quizalofop + 17% COC | 5 oz + 1% v/v | Post | 74.25 | b | a |
| 10 | Quizalofop + Scoil ® | 5 oz + 1% v/v | Post | 100.00 | a | a |
| 11 | Quizalofop + Sun-It II ® | 5 oz + 1% v/v | Post | 100.00 | a | a |
| 12 | Quizalofop + CL4769 | 5 oz + 1% v/v | Post | 100.00 | a | a |
| 13 | Quizalofop + CL7769 | 5 oz + 1% v/v | Post | 100.00 | a | a |
| 14 | Quizalofop + Preference ® | 5 oz + 0.25% v/v | Post | 100.00 | a | a |
| 15 | Quizalofop + Preference ® | 5 oz + 0.5% v/v | Post | 100.00 | a | a |
| 16 | Ouizalofop + X-77 ® | 5 oz + 0.25% v/v | Post | 100.00 | a | a |
| 17 | Fluzifop + Fenoxoprop + 17% COC | 6 oz + 1% v/v | Post | 100.00 | a | a |
| 18 | Fluzifop + Fenoxoprop + Scoil ® | 6 oz + 1% v/v | Post | 100.00 | a | a |
| 19 | Fluzifop + Fenoxoprop + Sun-It II ® | 6 oz + 1% v/v | Post | 100.00 | a | a |
| 20 | Fluzifop + Fenoxoprop + CL4769 | 6 oz + 1% v/v | Post | 100.00 | a | a |

TABLE 10B-continued

% Volunteer Corn Control

| | | | | 4 WAT | | |
|---|---|---|---|---|---|---|
| Treat | Herbicide Treatments | Rate/Acre | Time | Voco | Alpha = 0.05 | Alpha = 0.1 |
| 21 | Fluzifop + Fenoxoprop + CL7769 | 6 oz + 1% v/v | Post | 100.00 | a | a |
| 22 | Fluzifop + Fenoxoprop + Preference ® | 6 oz + 0.25% v/v | Post | 100.00 | a | a |
| 23 | Fluzifop + Fenoxoprop + Preference ® | 6 oz + 0.5% v/v | Post | 100.00 | a | a |
| 24 | Fluzifop + Fenoxoprop + X-77 ® | 6 oz + 0.25% v/v | Post | 100.00 | a | a |
| 25 | Clethodim + 17% COC | 4 oz + 1% v/v | Post | 98.50 | a | a |
| 26 | Clethodim + Scoil ® | 4 oz + 1% v/v | Post | 100.00 | a | a |
| 27 | Clethodim + Sun-It II ® | 4 oz + 1% v/v | Post | 99.50 | a | a |
| 28 | Clethodim + CL4769 | 4 oz + 1% v/v | Post | 100.00 | a | a |
| 29 | Clethodim + CL7769 | 4 oz + 1% v/v | Post | 100.00 | a | a |
| 30 | Clethodim + Preference ® | 4 oz + 0.25% v/v | Post | 95.50 | a | a |
| 31 | Clethodim + Preference ® | 4 oz + 0.5% v/v | Post | 94.25 | a | a |
| 32 | Clethodim + X-77 ® | 4 oz + 0.25% v/v | Post | 92.50 | a | a |
| | | | lsd = 0.5 | | 9.406 | |
| | | | lsd = .1 | | | 1.451 |
| | | | C.V. | 7.164 | | |

TABLE 11A

% Giant Foxtail Control

| | | | | 2 WAT | | |
|---|---|---|---|---|---|---|
| Treat | Herbicide Treatments | Rate/Acre | Time | Gift | Alpha = 0.05 | Alpha = 0.1 |
| 1 | Sethoxydim + 17% COC | 12 oz + 1% v/v | Post | 92.00 | ef | gh |
| 2 | Sethoxydim + Scoil ® | 12 oz + 1% v/v | Post | 97.25 | a–c | a–c |
| 3 | Sethoxydim + Sun-It II ® | 12 oz + 1% v/v | Post | 95.25 | a–e | b–f |
| 4 | Sethoxydim + CL4769 | 12 oz + 1% v/v | Post | 94.50 | b–f | c–g |
| 5 | Sethoxydim + CL7769 | 12 oz + 1% v/v | Post | 95.25 | a–e | b–f |
| 6 | Sethoxydim + Preference ® | 12 oz + 0.25% v/v | Post | 93.75 | d–f | d–h |
| 7 | Sethoxydim + Preference ® | 12 oz + 0.5% v/v | Post | 96.50 | a–d | a–d |
| 8 | Sethoxydim + X-77 ® | 12 oz + 0.25% v/v | Post | 93.25 | d–f | e–h |
| 9 | Quizalofop + 17% COC | 5 oz + 1% v/v | Post | 97.25 | a–c | a–c |
| 10 | Quizalofop + Scoil ® | 5 oz + 1% v/v | Post | 97.50 | ab | ab |
| 11 | Quizalofop + Sun-It II ® | 5 oz + 1% v/v | Post | 97.75 | ab | ab |
| 12 | Quizalofop + CL4769 | 5 oz + 1% v/v | Post | 98.00 | a | ab |
| 13 | Quizalofop + CL7769 | 5 oz + 1% v/v | Post | 96.00 | a–d | a–d |
| 14 | Quizalofop + Preference ® | 5 oz + 0.25% v/v | Post | 98.25 | a | a |
| 15 | Quizalofop + Preference ® | 5 oz + 0.5% v/v | Post | 98.25 | a | a |
| 16 | Quizalofop + X-77 ® | 5 oz + 0.25% v/v | Post | 98.00 | a | ab |
| 17 | Fluzifop + Fenoxoprop + 17% COC | 6 oz + 1% v/v | Post | 98.00 | a | ab |
| 18 | Fluzifop + Fenoxoprop + Scoil ® | 6 oz + 1% v/v | Post | 95.25 | a–e | b–f |
| 19 | Fluzifop + Fenoxoprop + Sun-It II ® | 6 oz + 1% v/v | Post | 95.25 | a–e | b–f |
| 20 | Fluzifop + Fenoxoprop + CL4769 | 6 oz + 1% v/v | Post | 97.25 | a–c | a–c |
| 21 | Fluzifop + Fenoxoprop + CL7769 | 6 oz + 1% v/v | Post | 97.25 | a–c | a–c |
| 22 | Fluzifop + Fenoxoprop + Preference ® | 6 oz + 0.25% v/v | Post | 97.25 | a–c | a–c |
| 23 | Fluzifop + Fenoxoprop + Preference ® | 6 oz + 0.5% v/v | Post | 98.00 | a | ab |
| 24 | Fluzifop + Fenoxoprop + X-77 ® | 6 oz + 0.25% v/v | Post | 98.00 | a | ab |
| 25 | Clethodim + 17% COC | 4 oz + 1% v/v | Post | 94.00 | c–f | d–h |
| 26 | Clethodim + Scoil ® | 4 oz + 1% v/v | Post | 94.50 | b–f | c–g |
| 27 | Clethodim + Sun-It II ® | 4 oz + 1% v/v | Post | 94.50 | b–f | c–g |
| 28 | Clethodim + CL4769 | 4 oz + 1% v/v | Post | 95.25 | a–e | b–f |
| 29 | Clethodim + CL7769 | 4 oz + 1% v/v | Post | 93.25 | d–f | e–h |
| 30 | Clethodim + Preference ® | 4 oz + 0.25% v/v | Post | 92.50 | ef | f–h |
| 31 | Clethodim + Preference ® | 4 oz + 0.5% v/v | Post | 94.50 | b–f | c–g |
| 32 | Clethodim + X-77 ® | 4 oz + 0.25% v/v | Post | 91.25 | f | h |
| | | | lsd = 0.5 | | 3.373 | |
| | | | lsd = .1 | | | 2.822 |
| | | | C.V. | 2.508 | | |

TABLE 11B

% Giant Foxtail Control

| Treat | Herbicide Treatments | Rate/Acre | Time | 4 WAT Gift | Alpha = 0.05 | Alpha = 0.1 |
|---|---|---|---|---|---|---|
| 1 | Sethoxydim + 17% COC | 12 oz + 1% v/v | Post | 81.25 | e–g | d–f |
| 2 | Sethoxydim + Scoil ® | 12 oz + 1% v/v | Post | 91.25 | a–e | a–c |
| 3 | Sethoxydim + Sun-It II ® | 12 oz + 1% v/v | Post | 86.25 | d–f | c–e |
| 4 | Sethoxydim + CL4769 | 12 oz + 1% v/v | Post | 94.25 | a–d | a–c |
| 5 | Sethoxydim + CL7769 | 12 oz + 1% v/v | Post | 73.75 | g | f |
| 6 | Sethoxydim + Preference ® | 12 oz + 0.25% v/v | Post | 80.00 | gf | ef |
| 7 | Sethoxydim + Preference ® | 12 oz + 0.5% v/v | Post | 80.00 | gf | ef |
| 8 | Sethoxydim + X-77 ® | 12 oz + 0.25% v/v | Post | 88.75 | b–f | b–d |
| 9 | Quizalofop + 17% COC | 5 oz + 1% v/v | Post | 98.50 | ab | a |
| 10 | Quizalofop + Scoil ® | 5 oz + 1% v/v | Post | 99.00 | a | a |
| 11 | Quizalofop + Sun-It II ® | 5 oz + 1% v/v | Post | 99.00 | a | a |
| 12 | Quizalofop + CL4769 | 5 oz + 1% v/v | Post | 98.75 | ab | a |
| 13 | Quizalofop + CL7769 | 5 oz + 1% v/v | Post | 98.25 | ab | a |
| 14 | Quizalofop + Preference ® | 5 oz + 0.25% v/v | Post | 97.75 | ab | a |
| 15 | Quizalofop + Preference ® | 5 oz + 0.5% v/v | Post | 98.50 | ab | a |
| 16 | Ouizalofop + X-77 ® | 5 oz + 0.25% v/v | Post | 96.50 | a–c | ab |
| 17 | Fluzifop + Fenoxoprop + 17% COC | 6 oz + 1% v/v | Post | 97.75 | ab | a |
| 18 | Fluzifop + Fenoxoprop + Scoil ® | 6 oz + 1% v/v | Post | 98.25 | ab | a |
| 19 | Fluzifop + Fenoxoprop + Sun-It II ® | 6 oz + 1% v/v | Post | 99.25 | a | a |
| 20 | Fluzifop + Fenoxoprop + CL4769 | 6 oz + 1% v/v | Post | 99.00 | a | a |
| 21 | Fluzifop + Fenoxoprop + CL7769 | 6 oz + 1% v/v | Post | 99.00 | a | a |
| 22 | Fluzifop + Fenoxoprop + Preference ® | 6 oz + 0.25% v/v | Post | 98.50 | ab | a |
| 23 | Fluzifop + Fenoxoprop + Preference ® | 6 oz + 0.5% v/v | Post | 98.25 | ab | a |
| 24 | Fluzifop + Fenoxoprop + X-77 ® | 6 oz + 0.25% v/v | Post | 99.25 | a | a |
| 25 | Clethodim + 17% COC | 4 oz + 1% v/v | Post | 86.50 | c–f | c–e |
| 26 | Clethodim + Scoil ® | 4 oz + 1% v/v | Post | 96.00 | a–d | ab |
| 27 | Clethodim + Sun-It II ® | 4 oz + 1% v/v | Post | 98.75 | ab | a |
| 28 | Clethodim + CL4769 | 4 oz + 1% v/v | Post | 97.25 | ab | ab |
| 29 | Clethodim + CL7769 | 4 oz + 1% v/v | Post | 90.75 | a–e | a–c |
| 30 | Clethodim + Preference ® | 4 oz + 0.25% v/v | Post | 93.50 | a–d | a–c |
| 31 | Clethodim + Preference ® | 4 oz + 0.5% v/v | Post | 91.50 | a–d | a–c |
| 32 | Clethodim + X-77 ® | 4 oz + 0.25% v/v | Post | 88.75 | b–f | b–d |
|  |  |  | lsd = 0.5 |  | 10.182 |  |
|  |  |  | lsd = .1 |  |  | 8.518 |
|  |  |  | C.V. | 7.75 |  |  |

Although the present invention has been described with reference to preferred embodiments, workers skilled in the art will recognize that changes may be made in form and detail without departing from the spirit and scope of the invention.

What is claimed is:

1. A methylated adjuvant comprising acidulated soybean soapstock having free fatty acids and neutral oil wherein at least about 95% of free fatty acids in the soapstock are methylated while neutral oils are unreacted.

* * * * *

UNITED STATES PATENT AND TRADEMARK OFFICE
CERTIFICATE OF CORRECTION

PATENT NO. : 5,495,033
DATED : February 27, 1996
INVENTOR(S) : HEMENDRA N. BASU, JOE V. GEDNALSKI, ROBERT W. HERZFELD It is certified that error appears in the above-indentified patent and that said Letters Patent is hereby corrected as shown below:

Col 17, Table 10A, line 16, delete "Ouizalofop", insert -- Quizalofop--

Col. 17, Table 10B, line 16, delete "Ouizalofop", insert -- Quizalofop--

Col. 18, Table 10B, line 3, under the heading "Voco", delete "95.25; under the heading "Alpha 0.05 a-e"; under the heading "Alpha 0.1" delete "b-f"

Line 9, under the heading "Voco", delete "74.25, insert --100.00--

Line 9, under the heading "Alpha = 0.05", delete "b", insert --a--

Line 9, under the heading "Alpha = 0.1", insert --a--

Col. 19, Table 11A, line 16, delete "Ouizalofop", insert -- Quizalofop--

UNITED STATES PATENT AND TRADEMARK OFFICE
CERTIFICATE OF CORRECTION

PATENT NO. : 5,495,033
DATED : February 27, 1996
INVENTOR(S) : HEMENDRA N. BASU, JOE V. GEDNALSKI, ROBERT W. HERZFELD It is certified that error appears in the above-indentified patent and that said Letters Patent is hereby corrected as shown below:

Col. 21, Table 11B, line 16, delete "Ouizalofop", insert -- Quizalofop--

Signed and Sealed this

Third Day of September, 1996

Attest:

BRUCE LEHMAN

Attesting Officer     Commissioner of Patents and Trademarks